United States Patent [19]

Cramer

[11] 4,325,950

[45] Apr. 20, 1982

[54] PLATINUM CAFFEINE CHLORIDE ANION COMPLEX AND METHOD

[75] Inventor: Roger E. Cramer, Honolulu, Hi.

[73] Assignee: The Research Corporation of the University of Hawaii, Honolulu, Hi.

[21] Appl. No.: 122,144

[22] Filed: Feb. 19, 1980

[51] Int. Cl.³ .................... A01N 9/00; A61K 31/555; A61L 13/00
[52] U.S. Cl. .................................... 424/245; 544/225
[58] Field of Search .................... 260/429 R; 424/245; 544/225

[56] References Cited

U.S. PATENT DOCUMENTS 4,169,846 10/1979 Kidani et al. ...................... 424/287

OTHER PUBLICATIONS

Connors et al., Platinum Coordination Complexes in Cancer Chemotherapy, Springer-Verlag, N.Y, pp. 21, 23, 46–52, 64, 65 (1974).

*Primary Examiner*—Helen M. S. Sneed
*Attorney, Agent, or Firm*—James C. Wray

[57] ABSTRACT

A platinum caffeine chloride anionic complex is formed by reacting $K_2PtCl_4$ with caffeine in an aqueous solution at neutral pH under ambient conditions of temperature and pressure. This complex is particularly useful for cancer treatment.

9 Claims, No Drawings

PLATINUM CAFFEINE CHLORIDE ANION COMPLEX AND METHOD

FIELD OF THE INVENTION

This application relates to formation of a platinum-amino complex and particularly to the formation of a platinum[caffeine] Cl$_3$ complex anion. Particularly, this application relates to the treatment of cancer with this complex.

BACKGROUND OF THE INVENTION

The anti-cancer activity of cis Pt(NH$_3$)$_2$Cl$_2$ is well documented and, is believed to result not from prevention of DNA replication but from damage to the DNA producing faulty replication. Damaged DNA is repaired by various DNA repair enzymes. It thus follows that if an agent such as cis Pt(NH$_3$)$_2$Cl$_2$ which damages DNA is administered along with another agent which inhibits a DNA repair enzyme, then the kill of cancerous cells will be greatly enhanced.

Caffeine is an inhibitor of DNA repair and it has been shown in cell culture studies that caffeine greatly increases cell kill caused by cis Pt(NH$_3$)$_2$Cl$_2$. While these cell culture studies have been demonstrably successful in vitro, they have not been successfully replicated in vivo, i.e., no enhancement of anti-cancer activity occurs when these compounds are combined.

Relevant references describing the effect of the Pt(NH$_3$)$_2$Cl$_2$ and caffeine are:

| Author | Title | Number |
|---|---|---|
| Van Den Berg, H. W. | Synergism Between the Antitumor Agent cis Platinum (II) Diamminedichloride and Caffeine: Toxicological and Molecular Studies (abstract) | 75-4316 |
| Van Den Berg, H. W. | Post-Republican Repair of DNA in Chinese Hamster Cells Treated with Cis Platinum (II) Diamine Dichloride, Enhancement of Toxicity and Chromosome Damage by Caffeine | 76-4670 |

It was theorized that the difference between in vivo and in vitro reactions may have been due to solubility and membrane transport properties and that, if the caffeine molecule could be complexed in such a way that these properties would be enhanced, the successful anti-cancer composition could be produced.

SUMMARY OF THE INVENTION

It has now been discovered that an anionic, heavy metal-containing caffeine complex can be prepared by reacting caffeine with K$_2$PtCl$_4$. This reaction is carried out at essentially a neutral pH, i.e., between 6 and 8, and at ambient temperatures and pressures for several days. The product is an easily dissociated potassium salt of Pt(caffeine)Cl$_3$.

The caffeine complex differs from all other known compounds of Pt which have anti-cancer activity in several aspects. First, all analogues of cis Pt(NH$_3$)$_2$Cl$_2$ contain two saturated amines in cis positions. These amines may be part of a chelate. These compounds also contain either two anions or a bidentate chelating ion with a −2 charge which always produce Pt complexes which are uncharged. The complex formed with caffeine, contrarily, has a −1 charge, contains three anions bound to Pt and, perhaps most importantly, has no possibility for cis and trans isomers. It is thus highly likely that the complex of this invention acts by an entirely different mechanism than previously known Pt-containing anti-tumor agents.

EXAMPLE 1

The complex of the subject invention was prepared by combining a 1:1 molar ratio of caffeine with K$_2$PtCl$_4$ in aqueous solution under conditions of ambient temperature and pressure for a period of several days. The solution was concentrated by evaporation and filtered utilizing filter paper and a mild vacuum. The resultant precipitate was a highly soluble yellow-orange powder.

The complex was then injected intraperitoneally to white mice according to the standards set forth in the P388 Lymphocytic Leukemia Test System used by the National Cancer Institute. All of the test conditions used in this example parallel those of that test. When compared with the control, the life span of the treated mice was increased from 10 days to from 15 to 24 days.

These values compare favorably with those obtained elsewhere utilizing the same cancer and cancer test procedure and the common cancer drug cis Pt(NH$_3$)$_2$Cl$_2$. As examples, the composition of the invention is administered orally, intraperitoneally, intravenously, or intramuscularly. In further examples the composition is used in combination with other drugs. This latter composition increased the life span from 17 to 20 days.

It is apparent, therefore, that the complex of this invention is at least equal to and may actually be superior to a known cancer-fighting drug.

It is also apparent that, because the composition of this invention reacts in ways currently unknown but apparently not identical to previous mechanisms, the complex of the subject invention may be used in combination with other anti-cancer drugs to further enhance the anti-cancer activity of the particular treatment.

I claim:

1. The complex comprising the potassium salt of Pt[caffeine] Cl$_3$.

2. A method for preparing Pt[caffeine] Cl$_3$ compound comprising reacting K$_2$PtCl$_4$ with caffeine in an aqueous solution while maintaining pH near neutrality under time-temperature conditions sufficient to form Pt[caffeine] Cl$_3$ and potassium chloride.

3. A method for treating P388 Lymphocylic Leukemia in mice comprising administering an effective amount of the potassium salt of Pt[caffeine] Cl$_3$ to a leukemic subject.

4. The method of claim 3 in which the potassium salt of Pt[caffeine] Cl$_3$ is administered in combination with another anticancer agent.

5. A composition for treating P388 Lymphocylic Leukemia in mice comprising the potassium salt of Pt[caffeine] CL$_3$ and a carrier.

6. The method of claim 3 wherein the composition is administered orally.

7. The method of claim 3 wherein the compound is administered intraperitoneally.

8. The method of claim 3 wherein the compound is administered intravenously.

9. The method of claim 3 wherein the compound is administered intramuscularly.

* * * * *